United States Patent [19]

Pawelek

[11] Patent Number: 5,216,116
[45] Date of Patent: Jun. 1, 1993

[54] SOLUBLE MELANIN

[75] Inventor: John M. Pawelek, Hamden, Conn.

[73] Assignee: Yale University, New Haven, Conn.

[21] Appl. No.: 525,944

[22] Filed: May 18, 1990

[51] Int. Cl.$^5$ ............................................ C08G 63/06
[52] U.S. Cl. .................................... 528/207; 435/41; 424/59; 424/63
[58] Field of Search .................... 424/59, 63; 528/207; 435/41

[56] References Cited

U.S. PATENT DOCUMENTS 5,017,194  5/1991  Arifoglu et al. .......................... 8/111

OTHER PUBLICATIONS

Orlow et al., Pigment Cell Research 5:113-121 (1992).

Primary Examiner—Douglas W. Robinson
Assistant Examiner—Jean C. Witz

[57] ABSTRACT

A melanin that is soluble in an aqueous solution at a pH of at least 5 to 9 at a temperature of 0° to 100° C. The melanin is further characterized by being capable of being filtered through at least a 0.45 micron size filter. Still further, the melanin is characterized by having a molecular weight of greater than 10,000 kilodaltons. The melanin is useful for providing a naturally-appearing tan to mammalian skin and hair. The melanin is also useful for providing a sun-screen to mammalian skin and hair.

13 Claims, 2 Drawing Sheets

SOLUBLE MELANIN

BACKGROUND OF THE INVENTION

1. Field of the Invention

The present invention concerns the synthesis of soluble forms of melanin and their composition, and methods of using such compositions to provide a naturally-appearing tan to mammalian skin and hair and to provide a sun-screen.

2. BACKGROUND INFORMATION

In biology, melanins are heteropolymers consisting of L-dopa and its enzymatic derivatives. They are ubiquitous in living organisms and are produced throughout the zoological and botanical phyla. In mammalian skin, melanins are produced through enzymatic processes in specialized cells known as "melanocytes". Melanins are the pigments of mammalian skin and hair.

Mammalian melanins are highly insoluble and can be dissolved (solubilized) only through non-physiological treatments such as boiling in strong alkali, or through the use of strong oxidants such as hydrogen peroxide. Tyrosinase, a key enzyme in the melanin biosynthetic pathway, can catalyze the formation of melanin in a test tube using L-tyrosine, L-dopa or 5',6'-dihydroxyindole as substrates, however, the product is an insoluble precipitate as described above.

It would be of commercial value to have forms of melanin which are soluble at physiological pH and temperature. Such melanins could be applied evenly to mammalian skin and hair in appropriate vehicles without any of the caustic side-effects arising from the harsh reagents needed to solubilize precipitated melanins.

Such solubilized melanins could impart a naturally-appearing tan to mammalian skin and hair. Solubilized melanins would also be effective as sun-screens, since melanins are the chemicals in the skin which absorb ultraviolet radiation and thus provide protection from its harmful effects, such as premature skin aging and the occurrence of skin cancers.

SUMMARY OF THE INVENTION

It is the object of the present invention to provide solubilized forms of melanin at physiological pH and temperatures.

It is another object of the present invention to provide compositions and methods for applying such melanins to mammalian skin and hair to provide a naturally-appearing tan.

It is another object of the present invention to provide compositions and methods for applying such melanins to mammalian skin and hair to provide a sun-screen.

The above objects and other objects, aims, and advantages are satisfied by the present invention. The present invention relates to a melanin that is soluble in aqueous solution, e.g., water or an aqueous buffered solution, at a pH of at least 5 to 9, preferably 6.5 to 7.5, at a temperature of 0° to 100° C. The soluble melanin is further characterized by being capable of being filtered through at least a 0.45 micron size filter.

The present invention also concerns a method of producing solubilized melanin comprising combining in a reaction mixture 5,6-dihydroxyindole and one or more enzymes derived from biological cells or tissues which have a pigmentary system. The reaction mixture may further comprise one or more of the following: L-dopa, 5,6-dihydroxyindole-2-carboxylic acid and dopachrome. The reaction mixture may still further comprise indole-5,6-quinone and/or melanochrome.

DETAILED DESCRIPTION OF THE INVENTION

Figure 1:
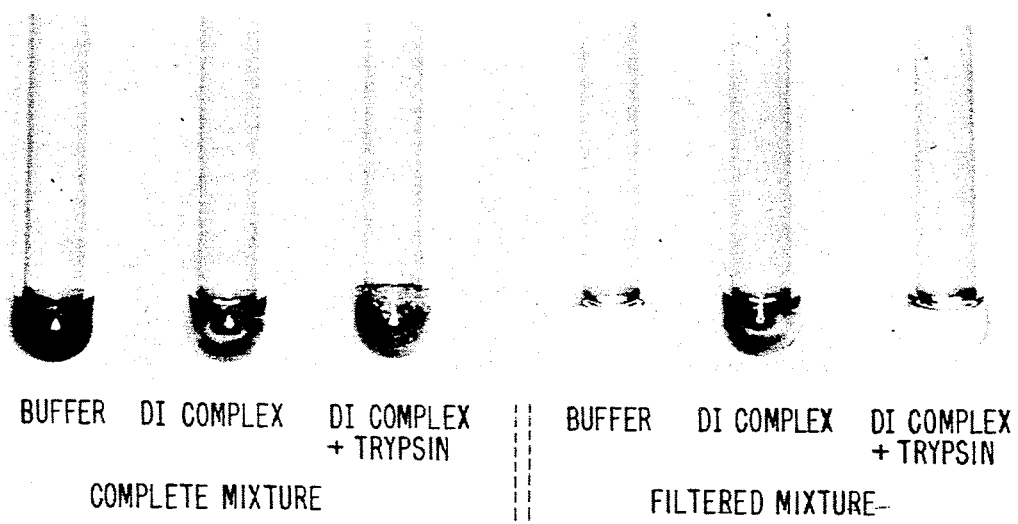
FIG. 1 depicts a photograph showing the enzymatic formation of soluble melanin according to the invention.

The soluble melanin of the invention remains in aqueous solution, at neutral pH (e.g., pH of 5 to 9, preferably 6.5 to 7.5), for long periods of time, e.g., indefinitely, at temperatures of 0° C. to 100° C., e.g., room temperature. The soluble melanin according to the invention is further characterized by remaining soluble upon freezing/thawing. The inventive soluble melanin is also characterized by being capable of being filtered through at least a 0.45 micron size filter. The soluble melanin according to the invention can be precipitated by strong acid.

Following enzymatic synthesis, the soluble melanin cannot be dialyzed through a semi-permeable membrane which allows the passage of molecules less than a molecular weight of approximately 10,000 kilodaltons. Therefore the soluble melanin according to the invention is of a molecular weight greater than 10,000 kilodaltons, however, this is not an essential characteristic for its usefulness. The soluble melanin can be lyophilized to a dry powder form and then reconstituted to its soluble form with distilled water or suitable aqueous solvents, e.g., sodium phosphate 0.1M or sodium chloride 0.1M.

The soluble melanin according to the invention is preferably prepared enzymatically, although synthetic means can also be used. The enzymatic preparation according to the invention comprises combining in a reaction mixture a substrate, i.e., 5,6-dihydroxyindole, and one or more enzymes derived from biological cells or tissues which contain a pigmentary system and more particularly have the ability to produce melanin. The reaction mixture may further comprise as a substrate one or more of the following: L-dopa, dopachrome and 5,6-dihydroxyindole-2-carboxylic acid. The reaction mixture may still further comprise as a substrate indole-5,6-quinone and/or melanochrome.

The individual components of the substrate, be it one component, i.e., 5,6-hydroxyindole or more than one component, preferably will be in an amount of 0.01 to 5.0 millimolar. Stated otherwise, if more than one component, i.e., more than 5,6-dihydroxyindole is used, the components will preferably be in equal proportions.

The combining in the reaction mixture is preferably conducted at a temperature of 15° C. to 37° C.

Structural formulas and the relationship among some of the above described compounds are depicted as follows:

Scheme I

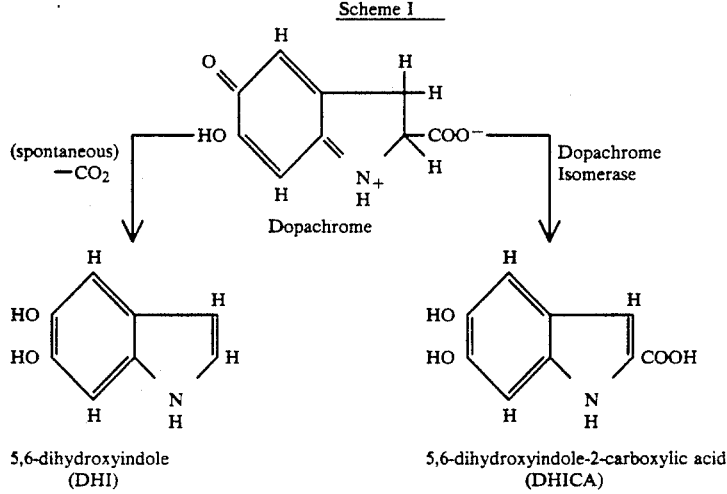

Scheme II

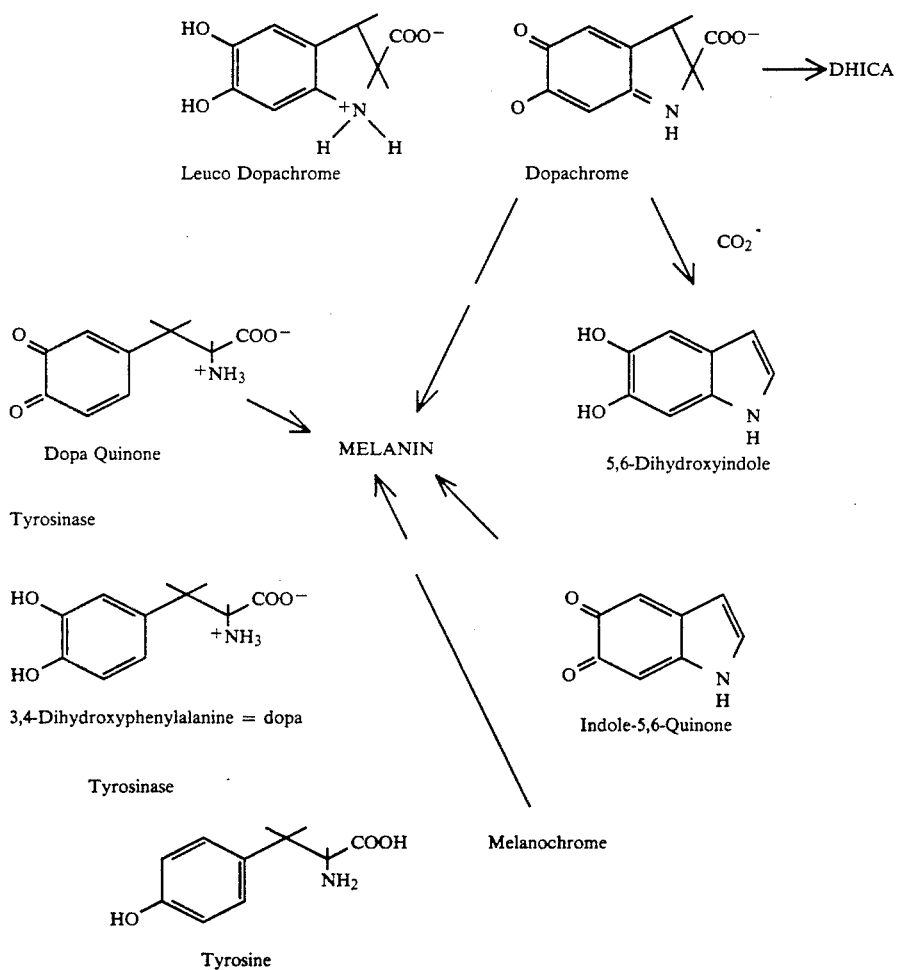

From the above it is seen that dopa quinone, leuco dopachrome, dopachrome, DHICA, 5,6-dihydroxyindole, indole-5,6-quinone, and melanochrome are all derivatives of dopa. Dopa itself is a derivative of tyrosine, so the above compounds are also derivatives of tyrosine (see Scheme II). Scheme I shows that dopachrome can give rise to 5,6-dihydroxyindole in a spontaneous non-enzymatic recation, or it can give rise to DHICA in anenzymatically catalyzed reaction. The enzyme which catalyzes dopachrome to DHICA is named dopachrome isomerase and may indeed be the enzyme responsible for soluble melanin formation. The enzyme may also be a part of a complex comprising tyrosinase, dopachrome isomerase, glycoprotein 75, MSH receptor and other unknown proteins.

The above described enzymes are described in the following papers:

tyrosinase: Ann Korner and John Pawelek, "Mammalian Tyrosinase Catalyzes Three Reactions in the Biosynthesis of Melanin", *Science*, 217:1163–1165, 1982; dopachrome isomerase: John Pawelek, "Dopachrome Conversion Factor Functions as an Isomerase", *Biochemical and Biophysical Research Communications*, 166:1328–1333, 1990; glycoprotein 75: Timothy M. Thomson, M. Jules Mattes, Linda Roux, Lloyd Old and Kenneth O. Lloyd, "Pigmentation-associated Glycoprotein of Human Melanomas and Melanocytes: Definition with a Mouse Monoclonal Antibody", *J. Invest. Derm.*, 85:169–174, 1985;

MSH receptor: Seth J. Orlow, Sara Hotchkiss, and John M. Pawelek, "Internal Binding Sites for MSH: Analyses in Wild-Type and Variant Cloudman Melanoma Cells", J. Cellular Physiology, 142:129–136, 1990.

The enzyme may also include dopachrome isomerase and one or more of glycoprotein 75, MSH receptor and tyrosinase.

The enzyme may take the form of one or more individual enzymes or a complex of enzymes including tyrosinase, dopachrome isomerase, glycoprotein 75, MSH receptor and one or more additional enzymes which are distinct from the aforesaid four described enzymes, but which are capable of catalyzing the synthesis of soluble melanin.

The soluble melanin according to the present invention can be admixed with a physiologically acceptable carrier to form a composition.

Physiologically acceptable carriers useful in the practice of the invention are known in the art and nonlimiting examples of such carriers include, for controlled release—microcapsules comprising carboxymethylene copolymers; for transdermal release—acrylamides and for topical application—cosmetic bases.

In addition, if desired, the composition according to this embodiment comprises at least one additive selected from the group consisting of solvents, fragrances, sunscreening agents, preservatives and chelating agents.

Cosmetic bases useful in the practice of the invention are well known and include lotions, creams, ointments and dusting powders. Examples thereof may be found in, e.g., U.S. Pat. Nos. 4,228,151; 4,282,206 and 2,949,403.

Solvents for use in accordance with the invention include, for example, ethanol, isopropyl alcohol, benzyl alcohol, oils, for example, ground nut oil, distilled and/or deionized water, physiological saline solution and the like. The specific solvent chosen will depend on the method of application.

It may also be desirable to add a preservative to the inventive compositions if they are to be used for topical applications. The preferred mode of administration of the inventive compositions is topical administration.

Preservatives are well known and may be exemplified by methylparaben, "DOWACIL 2000" and propylparaben.

If desired, in order to reduce the acidity or basicity of the inventive compositions, bases, acids or buffers may be added thereto in accordance with the knowledge of the art.

The concentration of soluble melanin in an aerosol, cream, lotion or other composition is preferably 0.01 mg/ml to 1.0 mg/ml.

Solutions have different colors depending on the concentration of "chromophore" dissolved in them. For example, a deep red solution will appear orange or pink when diluted with more solvent, but no additional chromophore. In the case of the soluble melanin, when it is dissolved at a fairly high concentration in water, e.g., 0.5 mg/ml, it appears brown-black in color. When more water is added so that the concentration of the soluble melanin is reduced to, e.g., 0.1 mg/ml, the solution appears golden in color. It is not believed that diluting the material changes any shift in the absorbance spectrum, rather it is believed to be a visual perception.

The invention will now be described with reference to the following non-limiting examples.

EXAMPLE 1

Source of Enzymes

The enzyme preparation for the synthesis of soluble melanin can be obtained from any biological cells or tissues which have the ability to produce melanin, for example:

(1) extracts of vertebrate skins from horses, cattle, sheep, pigs, or any other such mammalian source; extracts of skins of fish, amphibia, reptiles, birds, or any other such vertebrate source;

(2) extracts of any botanical source which has the ability to produce melanin, such as mushrooms, potatoes, bananas, or any other such botanical source;

(3) extracts of invertebrate organisms such as worms, arthropods, or any such invertebrate source which has the ability to produce melanin;

(4) extracts of any single-cell organisms which have the ability to produce melanin, but which do not necessarily fall into a category of zoological or botanical, such as bacteria and protozoans;

(5) extracts of any organisms in which genes for enzymes producing soluble melanin have been genetically cloned; and (6) culture media of any organisms or cells which secrete enzymes for producing soluble melanin—such organisms or cells may or may not express cloned genes for the enzymes.

Furthermore, the source of biological material for the isolation of enzymes to produce soluble melanin does not necessarily have to be actively synthesizing melanin in vivo. A pigmentary system is defined as all or part of a group of enzymes which can recognize as their substrates precursors and/or intermediates in the melanin biosynthetic pathway. Some biological sources contain a pigmentary system, but do not synthesize melanin, however, extracts derived from them can produce soluble melanin. These biological systems, in their living state, are referred to as "amelanotic", or "non-pigmented". Many albino organisms fall into this category, i.e., they possess an incomplete or inhibited pigmentary system and do not make melanin in vivo, however, extracts from some albino organisms contain enzymes that can produce soluble melanin. Such organisms are also potential sources of enzymes for the production of soluble melanins.

EXAMPLE 3

Preparation of Enzymes

The enzymes for production of soluble melanin can be isolated from an extract of an appropriate biological source, or, from the culture media should the enzymes be secreted into the media by the source (see Example 1). Extracts are prepared by lysing the cells of the biological source through procedures such as homogenization (e.g., in a common kitchen "blender", in appropriate glass, metal, or plastic tissue homogenizers); such as freeze-thawing in a hypotonic solution such as water; or by any means which disrupt the cellular wall or plasma membrane of the biological source. In cases where the enzymes for producing melanin are themselves insoluble (e.g., in a particulate form within the cells), it may be necessary to lyse the cells in the presence of a non-ionic detergent such as "TRITON X-100", "CHAPS", or "TWEEN 80", or an organic solvent such as acetone or ethanol, or any other solvents which solubilize the enzymes, without destroying their ability to produce soluble melanin.

The following procedures may be useful, but are not mandatory for the preparation:

Extracts containing the enzymes in a soluble form can be clarified by filtration through such material as gauze or filter paper; or by centrifugation; or by "settling" through the use of natural gravitational force.

Extracts can be further clarified by mixing them with calcium phosphate (also known as "hydroxylapatite") which is itself insoluble, but which attaches to many molecular structures in cells, but does not attach to the enzymes for preparation of soluble melanins. The calcium phosphate and its attached molecules can be removed from the extract by filtration, centrifugation, or gravitational settling as described above. Although calcium phosphate is useful in this regard, the procedure is not restricted to the use of this agent only. Any insoluble compound which attaches to molecular structures other than the enzymes in question and does not destroy the activity of the enzymes can be employed.

Extracts can be further clarified by mixing them with an anion exchange agent such as diethylaminoethyl cellulose. At conditions around neutral pH (e.g., pH 6.5-7.5) and low buffer concentration (e.g., 5-10 millimolar sodium phosphate), the enzymes for production of soluble melanin will attach to such an anion exchange agent, while many other molecular structures will not. The enzymes in question can then be eluted from the anion exchange agent by increasing the salt concentration (e.g., by adding 0.4 molar sodium chloride, or by using a gradient of sodium chloride from 0 molar to 0.4 molar). Although diethylaminoethyl cellulose, sodium phosphate, and sodium chloride are useful in this regard, the procedure is not restricted to the use of these agents only. Any anion exchange resin, buffer, or salt which does not destroy the activity of the enzymes in question can be employed. The principle is the same.

Extracts can be further clarified by mixing them with an agent which attaches to glycoproteins, such as wheat germ lectin-sepharose. In mammalian cells, the enzymes in question are glycoproteins and therefore attach to such lectins, while many other molecular structures do not. The enzymes in question can then be eluted from the lectin by mixing with an appropriate sugar such a N-acetylglucoseamine, which causes a displacement of the enzymes from the lectin. Although wheat germ lectin-sepharose, and N-acetylglucoseamine are useful in this regard, the procedure is not restricted to the use of these agents only. Any appropriate lectin or sugar which does not destroy the activity of the enzymes in question can be employed. The principle is the same.

Extracts can be further clarified by applying them to columns containing molecular sieves such as Sephadex columns, or high pressure liquid chromatography columns containing molecular sieves. The enzymes in question can be eluted from such columns with non-destroying buffers according to their molecular weights and can be thereby separated from other molecular structures with differing molecular weights. Although Sephadex columns and various HPLC resins are useful molecular sieves, the procedure is not restricted to the use of these agents only. Any appropriate method for separation of molecules according to their molecular weights which does not destroy the activity of the enzymes in question can be employed. When each of the above procedures is carried out in the sequence listed, a preparation is obtained which contains the following: tyrosinase, dopachrome isomerase, a protein designated "glycoprotein 75∞ or "gp75", which exhibits catalase activity, and a protein designated "MSH receptor". That is, these four known proteins co-purify through the above procedures. Analyses by polyacrylamide gel electrophoresis indicate that there may be ten or more proteins in total. It is not presently known which protein or combination thereof catalyzes the synthesis of soluble melanin, although the synthesis can occur in the presence of phenylthiourea, a potent inhibitor of tyrosinase, suggesting that tyrosinase may not be necessary.

EXAMPLE 3

Enzymatic Synthesis of Soluble Melanin

Soluble melanin is prepared by mixing the enzymes, isolated and purified as described above, with a solution containing 5,6-dihydroxyindole and all or some of the following components as substrates: L-dopa, dopachrome and 5,6-dihydroxyindole-2-carboxylic acid. The enzymes and the substrates are allowed to incubate in a non-destroying buffer (e.g., 0.1 molar sodium phosphate, pH 6.5-7.5) at ambient temperature or any suitable non-destroying temperature which allows for the reaction to occur (e.g., 15°-37° C.), until soluble melanins begin to appear (e.g., 3-6 hours). The reaction can be monitored visually or with the use of a spectrophotometer set in the visual spectrum (e.g., 400 millimicrons). When the reaction has reached completion, the salts from the buffer can be removed by dialysis and the soluble melanin can be stored at room temperature, frozen, or as a crystal or powder obtained through such procedures as natural evaporation or lyophilization. It is useful, but not mandatory, to enzymatically synthesize soluble melanin in the presence of a tyrosinase inhibitor such as phenylthiourea, because tyrosinase, which is occasionally present in the enzyme preparation, can cause the formation of insoluble melanin. Although phenylthiourea is a useful tyrosinase inhibitor because it does not inhibit or destroy the enzymes in question, the procedure is not restricted to phenylthiourea and any such tyrosinase inhibitor can be employed.

Soluble melanin prepared by the above procedure is golden-brown in color and absorbs widely throughout the ultraviolet and visible spectra (e.g., 220 to 700 millimicrons). The color can vary from brown-black in very concentrated solutions, to golden in more dilute solutions. The addition of sulfhydryl-containing compounds such as cysteine or glutathione can impart a reddish color to the soluble melanins.

FIG. 1 depicts the enzymatic formation of soluble melanin. The contents of the three tubes on the right were filtered through a 0.45 micron filter, otherwise they were identical in composition to the contents of the three tubes on the left. Considering the three tubes on the left:

1) The far left-hand tube contained a mixture of dopachrome, dopa, 5,6-dihydroxyindole, and 5,6-dihydroxyindole-2-carboxylic acid. It also contained the buffer used to dissolve the enzymes (sodium phosphate 5mM, pH 6.8, containing 20% glycerol vol/vol), but the enzymes themselves were not added.

2) The second tube from the left contained the same mixture as in the left-hand tube, but in addition it contained the enzymes dissolved in their buffer. The enzymes are referred to as "DI Complex".

3) The third tube from the left was identical to the middle tube, but also contained trypsin, a potent proteolytic enzyme, at a concentration of 0.5 mg/ml.

The three tubes on the left were incubated at room temperature for 6 hours before half their contents were removed and filtered as described above into the three right-hand tubes.

It can be seen that with buffer only, all the black melanin which formed was trapped on the filter, i.e., insoluble. When the DI Complex was added, the golden-brown melanin was completely filterable, i.e., soluble. When trypsin was present, no soluble melanin was formed, indicating that the soluble melanin production was catalyzed by a protein (enzyme).

The soluble melanins provided in Example 3 have the following characteristics:

(1) are greater than molecular weight 10,000,
(2) are stable to boiling,
(3) are stable to freezing,
(4) can be filtered through a filter at least as small as 0.45 microns,
(5) are soluble in water at a pH range of at least 6.5-7.5 at temperatures from 0°-100° C.,
(6) can be precipitated by strong acid,
(7) can be lyophilized to a crystal/powder form which can be redissolved in water,
(8) vary from brown-black to golden in color depending on concentration,
(9) absorb throughout the ultraviolet and visible spectra and
(10) can be prepared in a red form with the addition of sulfhydryl-containing compounds.

EXAMPLE 4

Spectrophotometric Quantitation of Soluble Melanin

Melanin was synthesized using a mixture of L-dopa, dopachrome, dihydroxyindole, and dihydroxyindole-2-carboxylic acid at concentrations of approximately 0.4 mg/ml dissolved in sodium phosphate, 0.1M, pH 6.8. The "DI Complex" enzymes purified approximately 2,000 fold from 0.5 grams mouse melanoma tissue (see Example 3) were dissolved in buffer (sodium phosphate, 5 mM, pH 6.8) and incubated in a 4 ml reaction mix with the above substrates at room temperature for 5 hours. The control reaction had buffer only, with no enzymes added. In both reactions, melanin formation occurred, but when the enzymes were present, the melanin could be filtered through a 0.45 micron filter, whereas in the presence of buffer only, the melanin was insoluble and could not be filtered. Solutions were diluted 50 fold before measuring the optical density. A photographic representation of this experiment is seen in FIG. 1.

Figure 2:
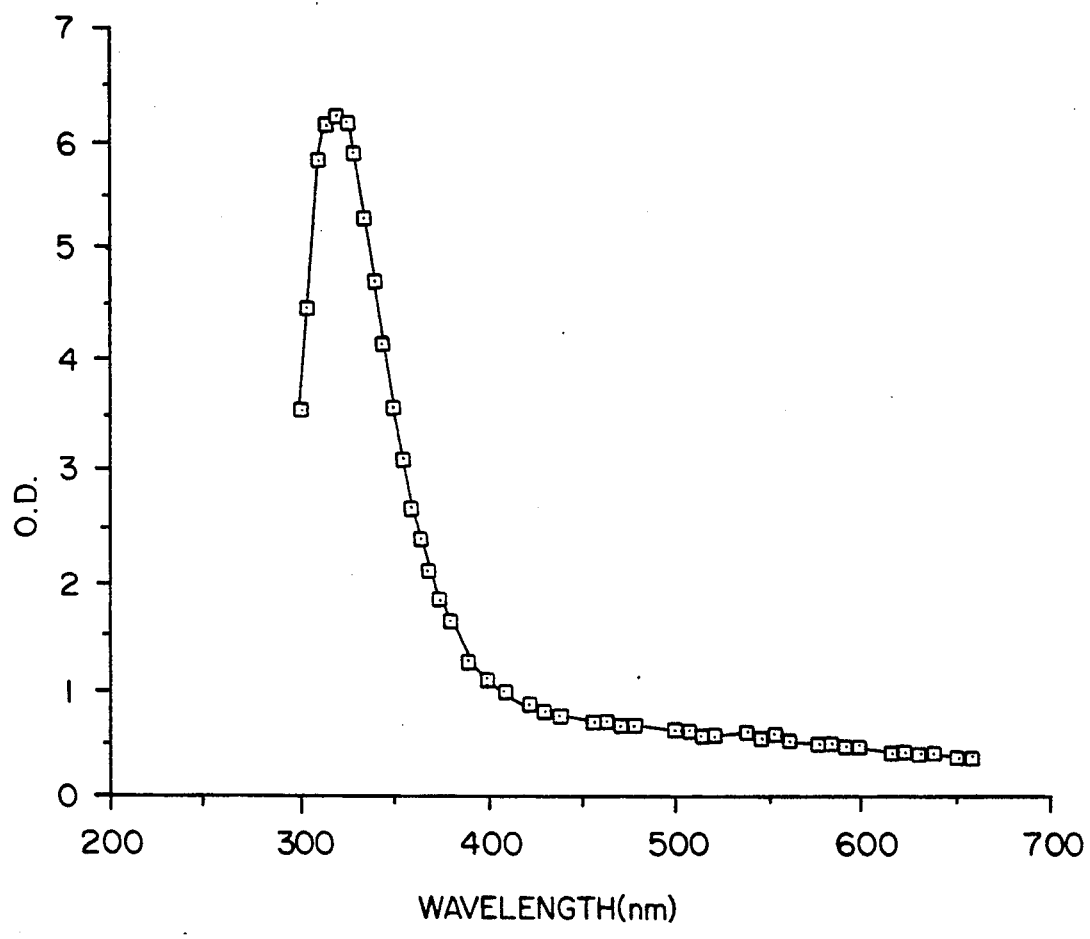
FIG. 2 depicts a graph showing the optical density (O.D.) of soluble melanin according to the invention at wavelengths greater than 300 nm.

FIG. 2 shows the optical spectrum of soluble melanin according to the present invention. The melanin exhibited a peak optical density (O.D.) at a wavelength of 310-320 nm. The spectra and O.D. were the same after the melanin had incubated under sterile conditions for 2 months at room temperature (20° C.), and whether or not the melanin was dialyzed or filtered through a 0.45 micron filter.

| Spectrophotometric Quanititation of Soluble Melanin | | |
|---|---|---|
| | Optical Density at Wavelength 320 nm | |
| Synthetic Route | Before Filtration | After Filtration |
| Buffer only (no enzymes added) | 1.22 | .024 |
| Enzymes added | 0.982 | 0.966 |

Example 5

Transdermal Release Composition

| | Parts by weight |
|---|---|
| Acrylamide copolymer (e.g., "polytrap FLME 203") | 20 |
| soluble melanin, as prepared according to Example 3 | 5 |
| Alcohol | 74.9 |
| and a fragrance | 0.1 |

The above mixture is applied to the skin, once a day, preferably in the morning, for two to four weeks.

EXAMPLE 6

Tanning Oil

A. An admixture is prepared by adding in the order indicated:

| | Parts by weight |
|---|---|
| decylolcate | 25.0 |
| isopropyl myristate | 15.0 |
| and propylene glycol dicaprylate/dicaprate | 5.0 |
| mineral oil | 54.85 |

B. An admixture is prepared by adding 0.01 pbw soluble melanin, e.g., as prepared as described in Example 3, to 0.01 pbw of "SOLERTAN PB-10"(a poly(propylene glycol) lanolin ether).

C. The admixture of part B is added to the admixture of part A and the resultant admixture is mixed until homogeneous.

D. The composition of part C is applied to the skin once or twice daily for two to four weeks.

EXAMPLE 7

Suntanning Lotion

An admixture was prepared containing the following:

| | Parts by weight |
|---|---|
| ICI G-1800 (e.g., poly[oxyethylene]21 stearyl ether) | 5.0 |
| isopropyl myristate | 10.0 |
| preservative | 0.1 |
| stearyl alcohol | 2.0 |
| 2-hydroxy-3,3,5-trimethylhexyl ester of benzoic acid | 8.0 |
| butylated hydroxyanisole | 0.05 |

The above mixture is heated to 70° C. and 60 parts by weight of water, preheated to 70° C. is added thereto. The resultant mixture is stirred and allowed to cool to room temperature.

To the above mixture is then added a 1% citric acid solution, QS, to achieve a pH of 5.0 after which 0.01 parts by weight of a soluble melanin, for example, as prepared according to Example 3, is added, as well as sufficient deionized water to yield 100 parts by weight of lotion.

The above lotion is applied to the skin one-half (½) hour prior to exposure to the sun. After swimming, sweating or toweling, as well as after each hour of exposure, the lotion is reapplied.

It will be appreciated that the instant specification is set forth by way of illustration and not limitation, and that various modification and changes may be made without departing from the spirit and scope of the present invention.

What is claimed is:

1. In the production of a soluble melanin by polymerizing a dihydroxyindole-carboxylio acid in an aqueous reaction medium, the improvement which comprises effecting the polymerization in the presence of a sulfhydryl compound.

2. The method according to claim 1 wherein the sulfhydryl compound comprises at least one of cysteine and glutathione.

3. The method according to claim 1, wherein the reaction mixture further comprises at least one of L-dopa, 5,6-dihydroxyindole-2-carboxylic acid and dopachrome.

4. The method according to claim 1, wherein the reaction mixture further comprises indole-5,6-quinone.

5. The method according to claim 1, wherein the reaction mixture further comprises melanochrome.

6. The method according to claim 1, wherein the reaction mixture further comprises indole-5,6-quinone and melanochrome.

7. The method according to claim 1, wherein the dihydroxyindole-carboxylic acid is produced enzymatically in situ.

8. A method according to claim 7, wherein the enzyme is derived from a biological cell or tissue which has the ability to produce melanin and wherein the enzyme extracted from said biological cell or tissue is contacted with an insoluble compound which purifies said enzyme by attaching to molecular structures other than the enzyme and does not destroy the activity of the enzyme.

9. A method according to claim 8, wherein the insoluble compound is calcium phosphate.

10. A method according to claim 7, wherein the enzyme is dopachrome isomerase.

11. A method according to claim 7, wherein the enzyme comprises dopachrome isomerase and at least one of glycoprotein 75 and MSH receptor.

12. A method according to claim 7, wherein the enzyme comprises a complex of tyrosinase, dopachrome isomerase, glycoprotein 75 and MSH receptor.

13. A method according to claim 7, wherein the enzyme comprises at least one individual enzymes or a complex thereof, said enzymes being selected from the group consisting of tyrosinase, dopachrome, isomerase, glycoprotein 75, MSH receptor, and at least one additional enzyme which is distinct from tyrosinase, dopachrome, isomerase, glycoprotein 75 and MSH receptor, and which enzyme is capable of catalyzing the synthesis of soluble melanin.

* * * * *